US008509384B2

(12) United States Patent
Spahn

(10) Patent No.: US 8,509,384 B2
(45) Date of Patent: Aug. 13, 2013

(54) METHOD FOR ENHANCED VISUALIZATION OF OBJECTS IN INTERVENTIONAL ANGIOGRAPHIC EXAMINATIONS

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 451 days.

(21) Appl. No.: 12/854,195

(22) Filed: Aug. 11, 2010

(65) Prior Publication Data

US 2011/0038458 A1  Feb. 17, 2011

(30) Foreign Application Priority Data

Aug. 12, 2009 (DE) .......................... 10 2009 037 243

(51) Int. Cl.
*H05G 1/64* (2006.01)
(52) U.S. Cl.
USPC .......................................... 378/98.12; 382/130
(58) Field of Classification Search
USPC ................................ 378/98.8, 98.12; 382/130
See application file for complete search history.

(56) References Cited

U.S. PATENT DOCUMENTS

| 4,459,990 | A  | * | 7/1984 | Barnea | 600/433 |
|---|---|---|---|---|---|
| 5,056,524 | A  | * | 10/1991 | Oe | 600/431 |
| 7,500,784 | B2 |   | 3/2009 | Grebner et al. | |
| 7,725,165 | B2 | * | 5/2010 | Chen et al. | 600/425 |
| 7,751,523 | B2 | * | 7/2010 | Ohishi | 378/4 |
| 8,175,357 | B2 | * | 5/2012 | Ozawa | 382/130 |
| 8,244,020 | B2 | * | 8/2012 | Chen et al. | 382/132 |
| 8,355,557 | B2 | * | 1/2013 | Chen et al. | 382/132 |
| 2007/0183637 | A1 |   | 8/2007 | Kreuzer et al. | |
| 2007/0201609 | A1 | * | 8/2007 | Ohishi et al. | 378/4 |
| 2008/0027316 | A1 |   | 1/2008 | Baumgart | |
| 2008/0101670 | A1 |   | 5/2008 | Baumgart et al. | |
| 2008/0137935 | A1 | * | 6/2008 | Spahn | 382/132 |
| 2008/0205591 | A1 | * | 8/2008 | Ozawa | 378/44 |
| 2009/0103682 | A1 | * | 4/2009 | Chen et al. | 378/98.12 |
| 2010/0002828 | A1 |   | 1/2010 | Miura | |
| 2010/0092061 | A1 | * | 4/2010 | Chen et al. | 382/132 |
| 2011/0038458 | A1 | * | 2/2011 | Spahn | 378/98.12 |
| 2011/0235889 | A1 | * | 9/2011 | Spahn | 382/132 |

FOREIGN PATENT DOCUMENTS

| DE | 102005062445 A1 | 7/2007 |
|---|---|---|
| EP | 2047800 A1 | 4/2009 |
| JP | 5122611 A1 | 5/1993 |
| JP | 2005295045 A1 | 10/2005 |

* cited by examiner

Primary Examiner — Thomas R Artman

(57) ABSTRACT

A method for enhanced visualization of objects in interventional angiographic examinations is provided. X-ray images are recorded during the system dose regulation phase with pure anatomy and during the filling phase with the vessels filled with contrast agent. A mask image is produced from both of the images. Native X-ray images are produced during a working or intervention phase with an object, for example a wire, a catheter or a "coil", moved in the vessel. The images have a matrix-shaped array of pixels. The pure anatomy images are subtracted from the filling images and from the native images for generating a first subtraction image and a second subtraction image respectively. The first and the second subtraction image are processed for generating a vessel image and an object image respectively. The vessel image and the object image are processed for generating a roadmap image which is played back on a monitor.

15 Claims, 6 Drawing Sheets

METHOD FOR ENHANCED VISUALIZATION OF OBJECTS IN INTERVENTIONAL ANGIOGRAPHIC EXAMINATIONS

CROSS REFERENCE TO RELATED APPLICATIONS

This application claims priority of German application No. 10 2009 037 243.1 filed Aug. 12, 2009, which is incorporated by reference herein in its entirety.

FIELD OF THE INVENTION

The invention relates to a method for enhanced visualization of objects during interventional angiographic examinations, for example a roadmap method in which firstly, in a first phase, X-ray images with pure anatomy are recorded during the system dose regulation phase and then, during a second phase, the filling phase, in which the vessels are filled with contrast agent, X-ray images are recorded, from both of which images the mask image is produced. In a third phase, a working or intervention phase, X-ray images are produced under fluoroscopy while an object, for example a wire, a catheter or a "coil", is moved in the vessel. Roadmap images are produced by means of subtraction and where appropriate further image processing techniques.

BACKGROUND OF THE INVENTION

For diagnostic examination purposes and for interventional procedures, for example in cardiology, radiology and neurosurgery, interventional X-ray systems are used for imaging whose typical major features can be, for example, a robot-controlled C-arm on which an X-ray tube and a X-ray detector are mounted, a patient examination table, a high-voltage generator for generating the tube voltage, a system control unit, and an imaging system including at least one monitor. A C-arm X-ray machine of said type, as illustrated in FIG. 1 for example, has a C-arm 2 which is rotatably mounted on a stand in the form of a six-axis industrial or articulated robot 1 and at the ends of which X-ray radiation source, for example an X-ray emitter 3 with X-ray tube and collimator, and an X-ray image detector 4 are mounted as the image recording unit.

By means of the articulated robot 1, known from U.S. Pat. No. 7,500,784 B2 for example, which preferably has six axes of rotation and consequently six degrees of freedom, the C-arm 2 can be moved arbitrarily in three dimensions, for example by its being rotated about a center of rotation between the X-ray emitter 3 and the X-ray detector 4. The inventive X-ray system 1 to 4 can be rotated in particular about centers of rotation and axes of rotation in the C-arm plane of the X-ray image detector 4, preferably about the axes of rotation intersecting the center point of the X-ray image detector 4 and the center point of the X-ray image detector 4.

The known articulated robot 1 has a base frame which is permanently installed on a floor, for example. Secured thereto is a turntable which is rotatable about a first axis of rotation. Attached to the turntable so as to be capable of pivoting about a second axis of rotation is a robotic floating link to which a robotic arm is fixed so as to be rotatable about a third axis of rotation. A robotic hand is attached to the end of the robotic arm so as to be rotatable about a fourth axis of rotation. The robotic hand has a securing element for the C-arm 2 which can be pivoted about a fifth axis of rotation and rotated about a sixth axis of rotation running perpendicular thereto.

The implementation of the X-ray diagnostic apparatus is not dependent on the industrial robot. Conventional C-arm devices can also be used. It is also possible to use bi-plane systems which consist, for example, of two C-arm X-ray machines as shown in FIG. 1.

The X-ray image detector 4 can be a flat semiconductor detector, rectangular or square in shape, which is preferably produced from amorphous silicon (a-Si). However, integrating and possibly counting CMOS detectors can also be used.

A patient 6 to be examined is positioned in the beam path of the X-ray emitter 3 on a patient examination table 5 as the examination object for the purpose of recording the heart, for example. Connected to the X-ray diagnostic apparatus is a system control unit 7 having an image system 8 which receives and processes the image signals of the X-ray image detector 4 (operator control elements, for example, are not shown). The X-ray images can then be studied on a monitor 9.

Important methods in imaging with C-arm X-ray machines are
diagnostic imaging with
  cardangiography at medium X-ray doses, a native visualization of the coronary vessels with the aid of contrast agents,
  digital subtraction angiography (DSA) for visualizing vessels exhibiting little movement with the aid of contrast agents, a method in which a native image is subtracted as what is termed a "mask" from a series of native images in which a vessel or vascular tree is filled with contrast agent, the anatomic background disappearing as a result of the subtraction and the vessel or vascular tree remaining visible on its own, and
  3D imaging with or without contrast agent and
interventional imaging with
  fluoroscopy or transillumination in which primarily the positioning of catheters, guide wires, balloon catheters, stents, etc. is effected using a small X-ray dose, this method also being used purely diagnostically in order to position a catheter for the application of contrast agent, and
  roadmapping, in which, similarly to DSA, initially a mask, a native image of a vascular tree filled with contrast agent, is produced. Next a series of native images is generated in which a wire, for example, is moved. For subtraction of the mask image all anatomical structures disappear. All that remain visible are the vascular tree and the wire moved "therein".

In addition to the methods mentioned here there are more advanced methods such as 3D roadmapping, for example.

In a known roadmap method, illustrated for example in FIG. 2, the following images are generated: a pure native image 10 (anatomy only) during the system dose regulation, a mask image 11, a native image from the fill phase in which the vascular tree 12 is filled with contrast agent, and a native image series 13 in which an object 14, a wire for example, is moved in the vascular tree 12 under fluoroscopy. From the fluoroscopy image series 13 in which the object 14 can be seen, the mask image 11 with vascular tree 12 filled with contrast agent is subtracted in a subtraction stage 15 and in an addition stage 16 a constant K for setting the mean grayscale value is added. Further image processing steps such as contrast adjustment, edge enhancement, etc. can follow until a current subtraction series 17 is obtained in which only the moving object 14 is still readily identifiable in the "frozen" vascular tree 12.

SUMMARY OF THE INVENTION

The object of the invention is to embody a method of the type cited in the introduction in such a way that during the roadmapping the traditional drawbacks such as poor visibility of the wire, "burnout" (disappearance of the wire, which is represented as dark, in the vascular tree, which is represented as light, due to excessively high contrast) etc. are reduced or avoided, and during an overlaying of a fluoroscopy image over a DSA image (overlay reference) in which the inverted DSA image is blended at a selectable percentage with a fluoroscopy image, the DSA image serving to visualize the vascular tree, the fluoroscopy serving to visualize the wire moved in the vascular tree, the visualization is improved.

The object is achieved according to the invention for a method and for a device by the features recited in the independent claims. Advantageous embodiments are disclosed in the dependent claims.

In the case of the above-mentioned method this is achieved by means of the following steps:

a) acquiring at least one empty image (pure anatomy), at least one filling image with vascular tree filled with contrast agent, and at least one native image with introduced object by means of a detector having a matrix-shaped array of pixels,
b) subtracting the empty and filling image in order to generate a first subtraction image,
c) subtracting the empty image and the at least one native image in order to generate at least one second subtraction image,
d) processing the first subtraction image in order to form a vessel image,
e) processing the at least one second subtraction image in order to form at least one object image,
f) processing the vessel image and the at least one object image in order to generate at least one roadmap image, and
g) playing back the at least one roadmap image.

In order to improve the visibility of wires, catheters, coils, etc. all three available images or image series are used:
(a) the pure native image (pure anatomy),
(b) the native image with contrast-agent-filled vascular tree as mask, and
(c) the native image with object.

In the roadmap method a mask image is subtracted from the current fluoroscopy series (native images with object), a constant grayscale value generally also being added to said mask image. This results in an image with mean grayscale value in which the vessel is represented as light and the wire as dark. An inverted representation could, of course, also be chosen. Further image processing steps such as filtering, in particular sharpening, edge enhancement or other grayscale value processing operations, such as in particular use of LUTs (look-up tables), can follow.

The mask image itself is generally produced from a series of images in which the fill level of the vascular tree is in different phases. The entire filled vascular tree can be represented by means of a minimum method in which the lowest grayscale value in each case from all of the images for each pixel is transferred into the corresponding pixel of the mask image.

An analogous procedure is followed with overlay reference. The generation of the pure vascular tree is known from DSA. In order to improve the visibility of the object, the extraction of the wire, the native image can be used at the beginning of the DSA sequence prior to application of the contrast agent as a pure native image (anatomy image). Now, however, the extracted wire can additionally be blended with the fluoroscopy image in order to enhance its visibility and the inverted DSA image blended at a certain percentage as in the case of the usual overlay reference procedure for vascular tree visualization.

As a further alternative to the previously described methods the mask image of a previously recorded DSA scene can be used as a mask for the roadmap, in which case it must be ensured that for this purpose the geometry, such as, for example, the angulation, the distance from radiation source to detector (SID=Source to Imager Distance), possibly also the selected zoom format, must be correct. Then an analogous procedure is followed as for the alternative roadmap method, although the DSA image takes the place of the vessel image and the native image from the DSA sequence takes the place of the native image 10.

The essentially novel aspect of the proposed method is to avoid the "washing out" of the contrast and promote the visibility of the object, wire or coil, irrespective of the intrinsic vessel contrast or the vessel contrast selected in the image processing. The idea is to represent the wire, for example, always with a permanently predefined grayscale value (generally deep black) even if the vessel in which the wire is located is represented as very light.

It has proven advantageous if the processing of the individual subtraction images according to steps d) and e) includes filtering, in particular sharpening, edge enhancement and/or other grayscale value processing operations, such as in particular the use of LUTs (look-up tables).

A first embodiment variant according to the invention is obtained if the processing of the vessel image and of the at least one object image according to step f) is a subtraction.

Alternatively, according to the invention, a sorting pass which performs a selection pixel by pixel can be executed as the processing of the vessel image in order to form the at least one object image according to step f).

It has proven advantageous if after the sorting pass a fourth image processing step is performed on the at least one roadmap image, the fourth image processing step being able to enhance contrast, suppress noise and/or increase sharpness.

Advantageously, the processing of the vessel image and of the at least one object image according to step f) can be a subtraction.

According to the invention an addition of a constant can be performed at least after one of the subtractions according to steps b), c) and f).

Advantageously, a binary operation, in particular threshold value forming or a segmentation, can be performed as the processing of the at least one second subtraction image for forming at least one object image according to step e).

According to the invention the method can be a roadmap method or a method for overlaying a fluoroscopy image over a DSA image (overlay reference).

It has proven advantageous if the processing of the vessel image and of the at least one object image according to step f) is a merging to form one optimal roadmap image having a fixed grayscale value, in particular black or colored.

The object is achieved according to the invention in the case of a device for performing the above-cited method by means of an angiographic X-ray system having a C-arm X-ray machine on the C-arm of which an X-ray emitter and an X-ray detector are arranged, having an image system for receiving the output signals of the X-ray detector, having storage means, and having a monitor for playing back the signals processed by the image system, in which the image system additionally has a first subtraction stage for subtracting the native image and the mask image in order to obtain a first subtraction image in which only the vascular tree can be distinguished, a first image processing step for improving the visibility of the vascular tree so that an optimal vessel image is obtained, a second subtraction stage for subtracting the native image and at least one of the native images of the fluoroscopy image series in order to obtain a second subtraction image in which only the object can be distinguished, a second image processing step for improving the visibility of the object so that at least one optimal object image is obtained, and a further image processing step for forming at least one roadmap image from the vessel image and the at least one object image.

According to the invention the third image processing step can include a third subtraction stage for subtracting the vessel image and at least one of the object images.

Alternatively the second image processing step can be embodied for performing a binary operation, in particular threshold value forming or a segmentation, and the third image processing step can be embodied for overlaying the vessel image and at least one of the binarily extracted object images.

It has proven advantageous if the image system additionally has addition stages downstream of the subtraction stages for the addition of a constant for setting the mean grayscale value.

BRIEF DESCRIPTION OF THE DRAWINGS

The invention is explained in more detail below with reference to exemplary embodiments shown in the drawing, in which.

DETAILED DESCRIPTION OF THE INVENTION

Figure 3:
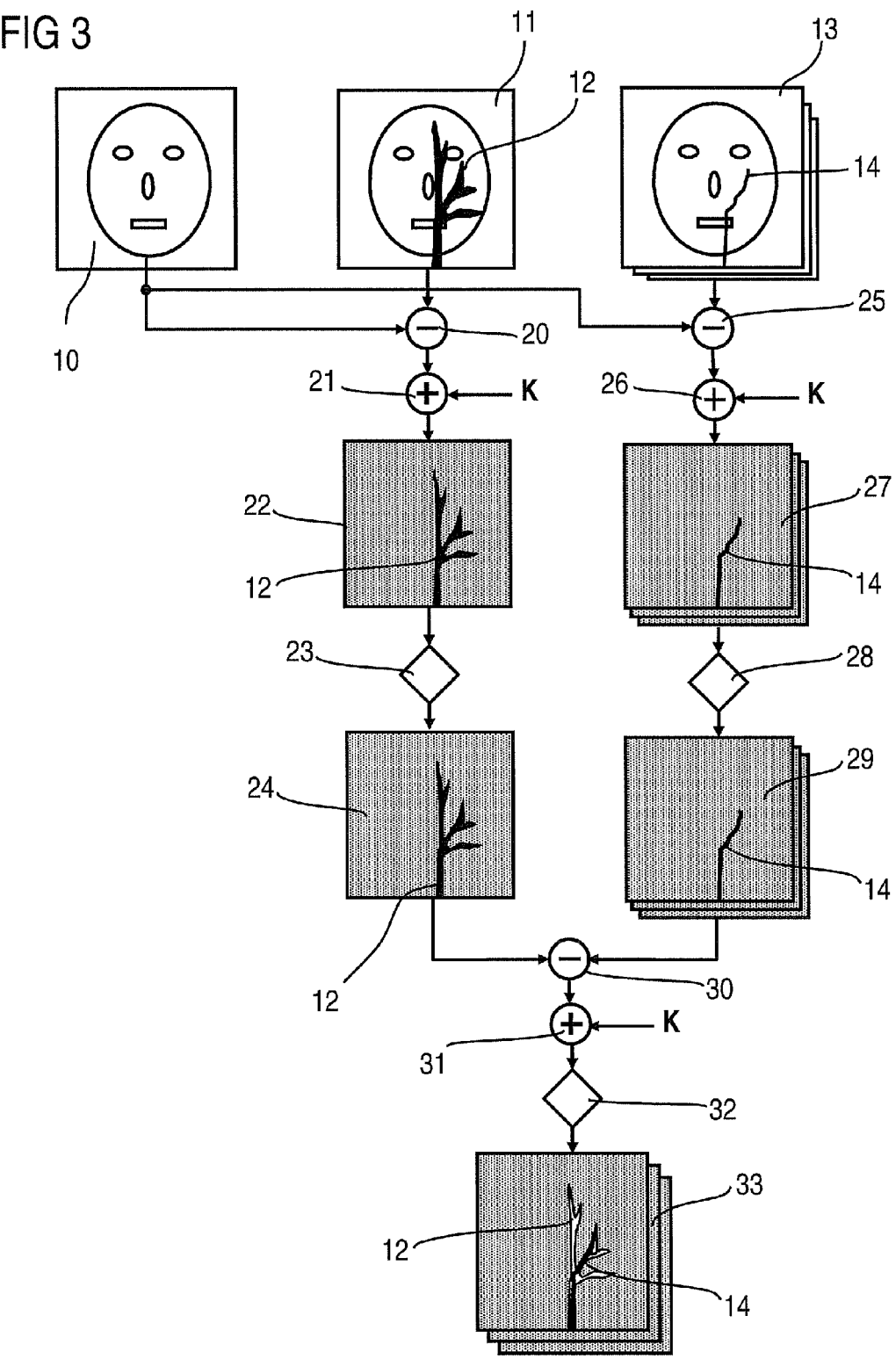
FIG. 3 shows a first embodiment variant of a roadmap method according to the invention.

FIG. 3 shows a first embodiment variant of a roadmap method according to the invention, wherein the following images are generated in a known manner: the pure native image 10 during the system dose regulation, the mask image 11 from at least one native image from the fill phase in which the vascular tree 12 is filled with contrast agent, and a native image series 13 in which an object 14, a wire for example, is moved in the vascular tree 12 under fluoroscopy.

According to the invention the native image 10 and the mask image 11 are now subtracted from one another in a first subtraction stage 20. In a first addition stage 21 a constant K for setting the mean grayscale value is added, such that a first subtraction image 22 is obtained in which only the vascular tree 12 can be distinguished. In a subsequent first image processing step 23 the visibility of the vascular tree 12 is improved such that an optimal vessel image 24 is obtained.

In parallel, in a second subtraction stage 25, the native image 10 and at least one of the native images of the image series 13 are subtracted from one another. In a second addition stage 26 a constant K for setting the mean grayscale value is added in turn, which constant can be different from the first constant K. By this means a second subtraction image 27 is obtained in which only the object 14 can be distinguished. In a following second image processing step 28 the visibility of the object 14 is improved such that at least one optimal object image 29 is obtained.

The vessel image 24 and the object image 29 are subtracted in a third subtraction stage 30 and in a third addition stage 26 a constant K for setting the mean grayscale value is added to the result, which constant can be different from the other constants K, such that optimal roadmap images 33 are obtained as a subtraction series.

Figure 4:
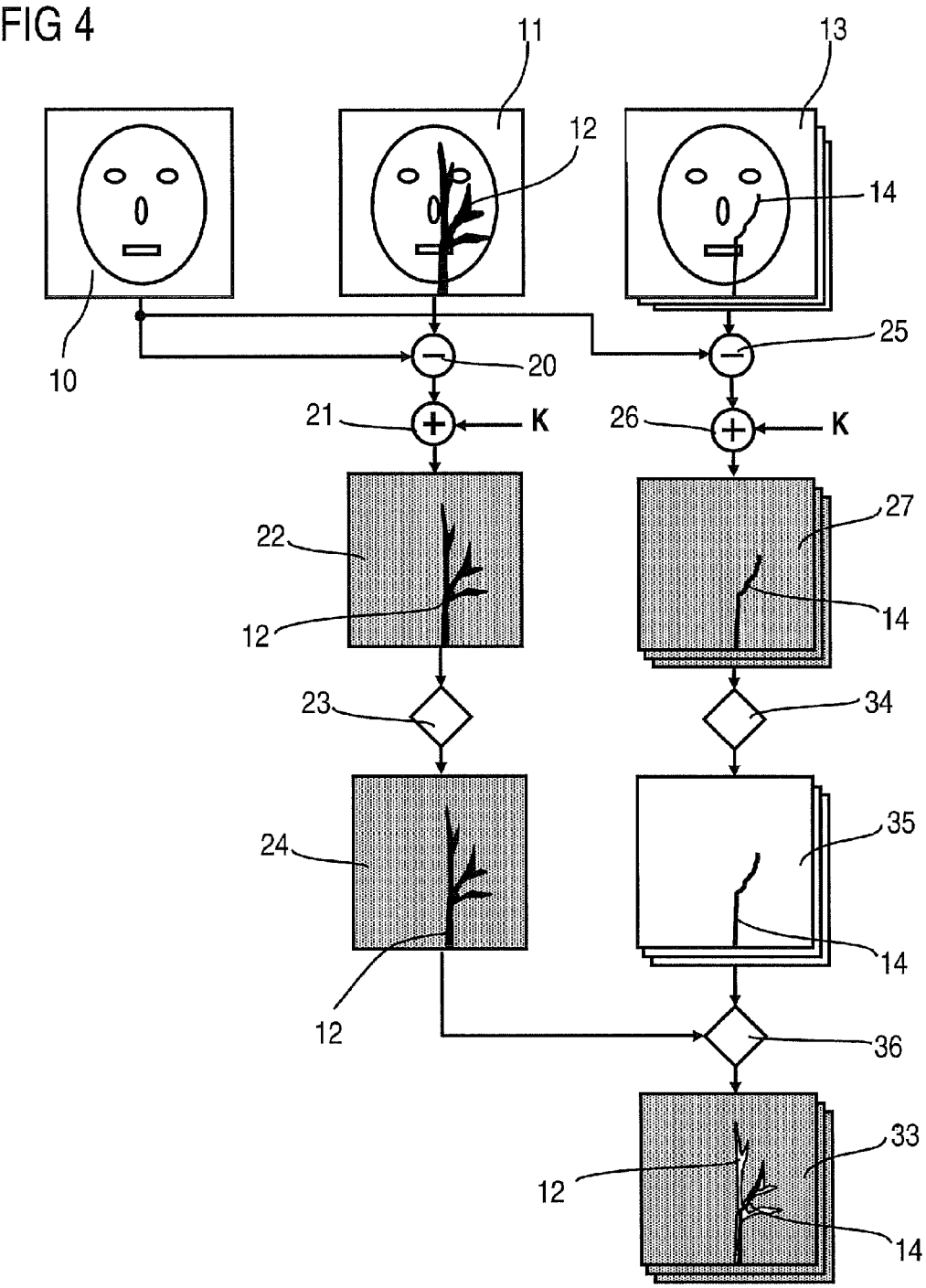
FIG. 4 shows a second embodiment variant of a roadmap method according to the invention.

FIG. 4 shows a second embodiment variant of the roadmap method according to the invention with binary extraction of the object (threshold value forming or segmentation) and fixed grayscale value representation in the roadmap image which is similar to the method described with reference to FIG. 3, for which reason the reference numerals are also retained for like blocks. The only difference is that a binary operation 34, a segmentation for example, is provided instead of the second image processing step 28, such that at least one binary object image 35 of the object 14 is generated. In a further image processing step 36 the vessel image 24 and the at least one binary object image 35 of the object 14 are merged, its being possible for a fixed value to be assigned to the object 14 of the binary object image 35. This can be a grayscale value or a color value.

In this embodiment of the roadmap method according to the second inventive method the object 14 is extracted binarily. When it is merged with the mask image 24 (vascular tree 12) this enables a visualization completely independently of the grayscale value distribution of the vascular tree 12 in the mask image 24 during the merging in the third image processing 36 in order to form an optimal roadmap image 33 with a fixed grayscale value, for example black or colored.

Figure 5:
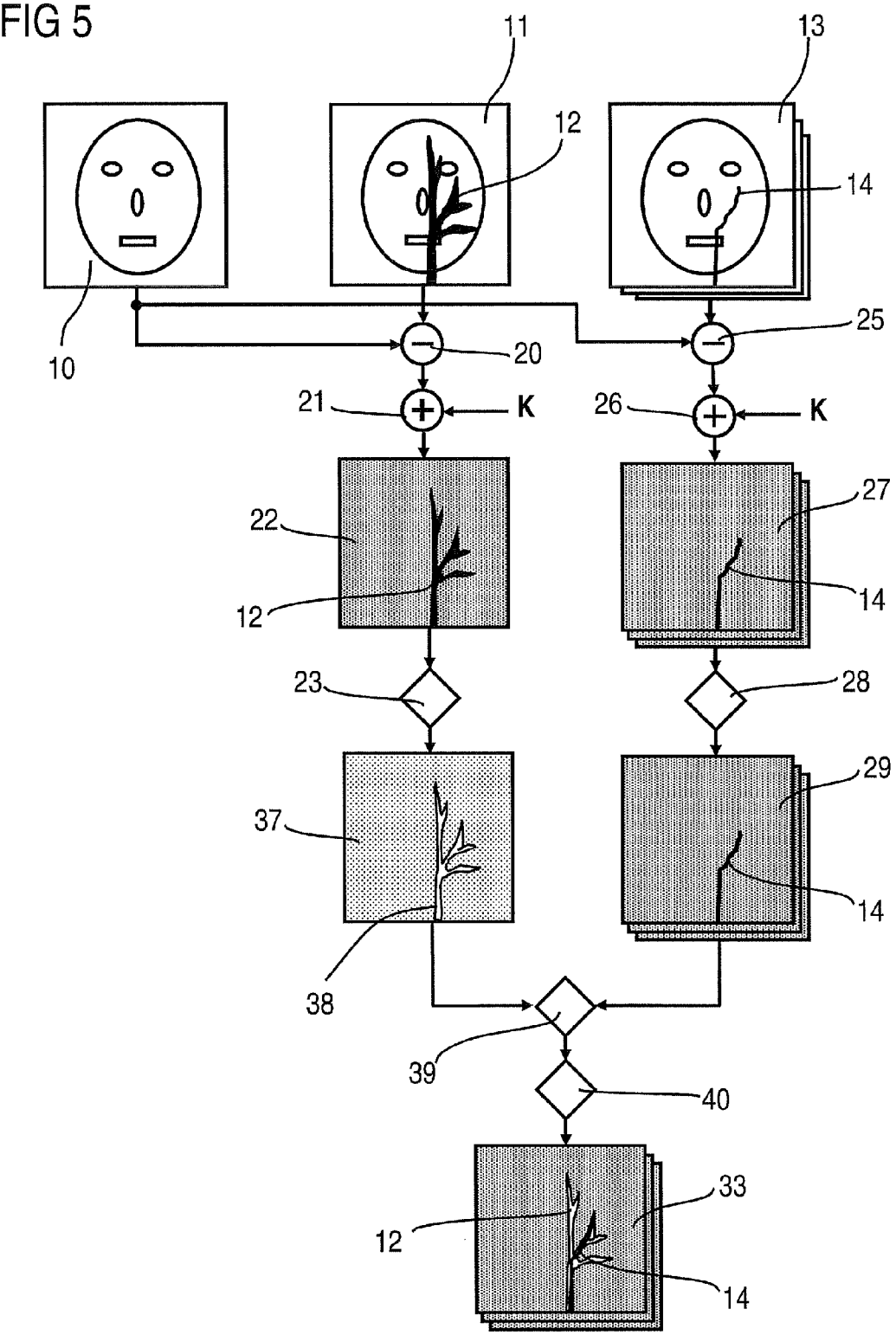
FIG. 5 shows a third embodiment variant of a roadmap method according to the invention after a new sorting method.

FIG. 5 shows a third alternative of the roadmap method according to the invention which is essentially similar to that described with reference to FIG. 3. The only difference is that the vessel image 24 and the object image 29 are not subjected to a subtraction, but are supplied to a sorting device 39 which performs a selection pixel by pixel.

The first prerequisite is that when a contrast agent is used the vessel image 24 is inverted, for example by mirroring the grayscale values around the constant K, with the result that an inverted vessel image 37 is obtained in which the inverted vascular tree 38 is represented as white. This inversion can be performed in the first image processing step 23, for example. If, on the other hand, the vessel is filled with $CO_2$, the blood in the vascular tree 38 is replaced and the vessel image 24 would, as shown, represent a light vascular tree 38; in that event an inversion would not be required.

The second prerequisite is that the mean values of both images, of the vessel image 24 and of the object image 29, are identical. This is ensured by the common added constant; otherwise the mean values must be adjusted.

The inverted vessel image 37 and the object image 29 are now analyzed pixel by pixel. It is investigated whether for each pixel (x,y) the grayscale value of the possibly inverted vessel image $G(x,y)$ and the grayscale value of the object image $O(x,y)$ lie above or below defined threshold values.

The following assignments are then made for the grayscale values of the resulting roadmap image R(x,y) 33:

If the object image O(x,y) 29 lies below the lower object threshold value $S_u$ (O), R(x,y) is assigned the value of the object image 29 O(x,y), irrespective of the value of G(x,y). As an alternative it could be required that G(x,y) simultaneously lies above the upper threshold $S_o$ (G).

If the inverted vessel image 37 G(x,y) lies above the upper threshold $S_o$ (G) and O(x,y) lies above the lower threshold $S_u$ (O), R(x,y) is assigned the value of the vessel image 37 G(x,y).

In all other cases the value of either G(x,y) or O(x,y) that lies closer to the constant, for example, or else a mean value of G(x,y) and O(x,y) can be chosen for R(x,y) Both methods help reduce the noise impression.

The threshold values are either predefined or determined from the current images 29 and 37. They are essentially correlated with the typical noise of the images. The upper and lower threshold values $S_o(G)$, $S_u(G)$ for G and So(O), Su(O) for O can be different, since the noise level in both images can be different.

The resulting roadmap image 33 R(x,y) is finally processed further, for example by enhancing the contrast, increasing the sharpness and/or suppressing noise, and displayed.

Figure 6:
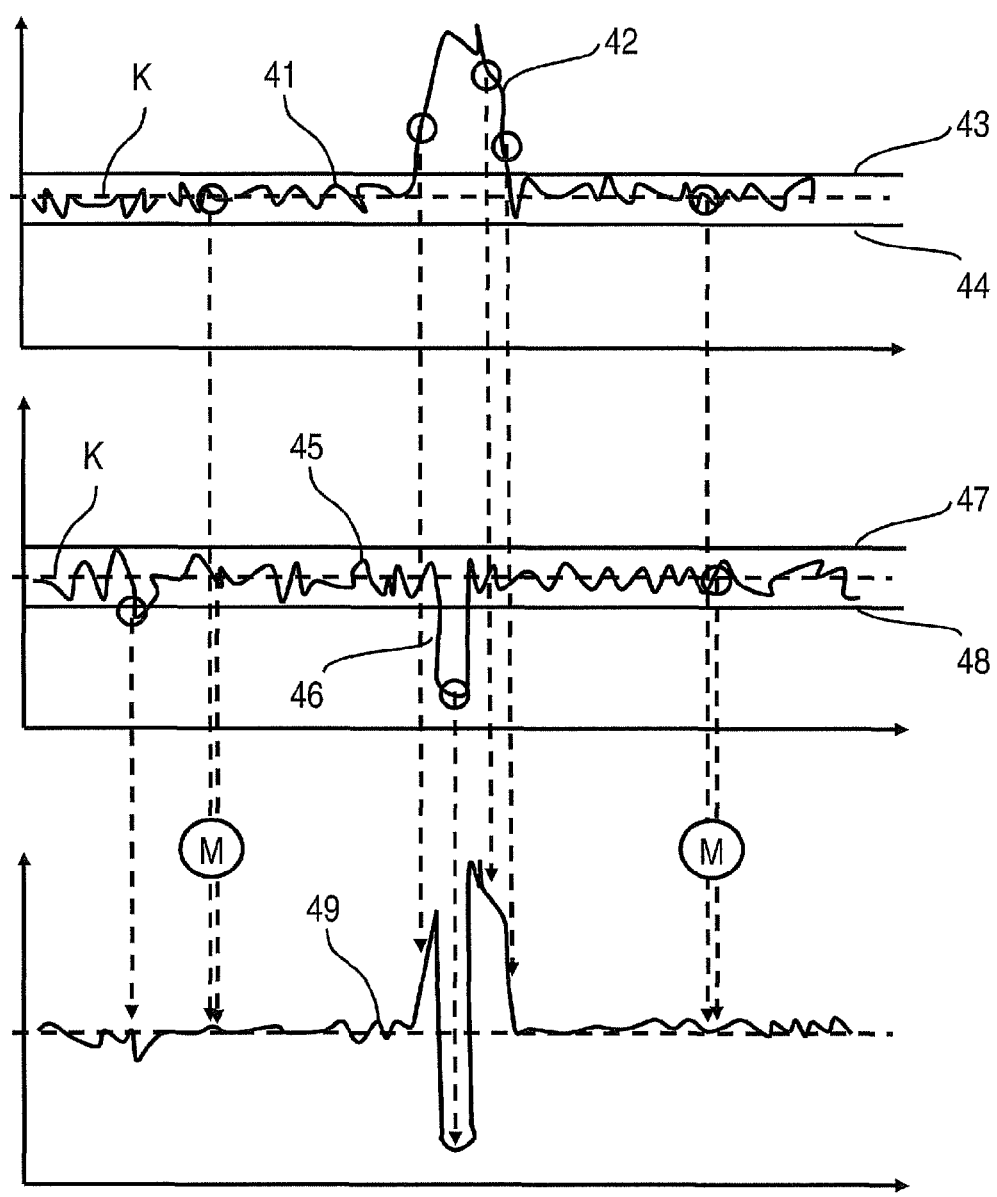
FIG. 6 shows line plots of the inverted vessel image G (top), of the object image O (center) and of the resulting roadmap image R (bottom) after a pixel-by-pixel ordering method.

FIG. 6 shows line plots of representative lines from the images. Line plot 41 of the inverted vessel image G is reproduced at the top with its upper vessel threshold value $S_o$ (G) 42 and lower vessel threshold value $S_u$ (G) 43. The vessel curve area 44 stands out clearly.

Line plot 45 of the object image O is shown in the center with its upper object threshold value $S_o(O)$ 46 and lower object threshold value $S_u$ (O) 47. Here, too, the object curve area 48 can be clearly distinguished.

Line plot 49, shown at the bottom, of the resulting roadmap image R was produced according to the inventive pixel-by-pixel ordering method in accordance with the aforementioned rules. Mean values of the pixel values from both images have been used at the points marked by "M".

The subject matter of the present patent application is to disclose improved methods for roadmapping in order to avoid traditional drawbacks such as poor visibility of the object, "burnout" (disappearance of the wire, which is represented as dark, in the vascular tree, which is represented as light, due to excessively high contrast, etc.), and overlay reference (overlaying of a fluoroscopy image over a DSA image). In the case of overlay reference the inverted DSA image is blended at a selectable percentage with a fluoroscopy image. The DSA image serves for visualizing the vascular tree, the fluoroscopy for visualizing the wire which is moved in the vascular tree.

In order to improve the visibility of objects 14, such as wires, catheters, coils, etc., for example, all three available images or image series are used:

(a) the pure native image 10 (pure anatomy),
(b) the native image with contrast-agent-filled vascular tree 12 (mask image 11), and
(c) the native image 13 (or the image series) with object 14.

Figure 1:
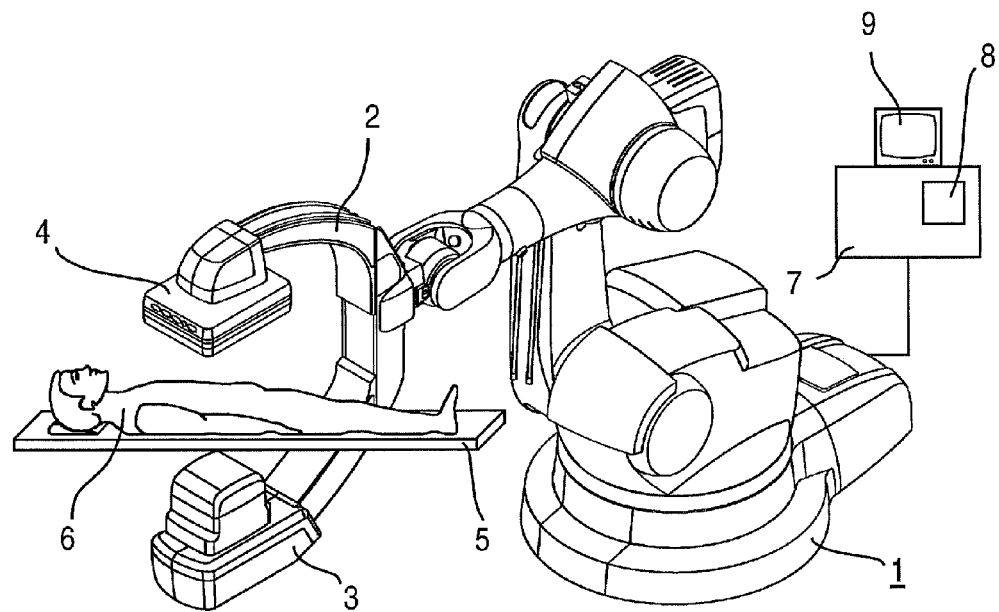
FIG. 1 shows a known X-ray C-arm system for radiology, cardiology or neurosurgery having an industrial robot as carrying device.
Figure 2:
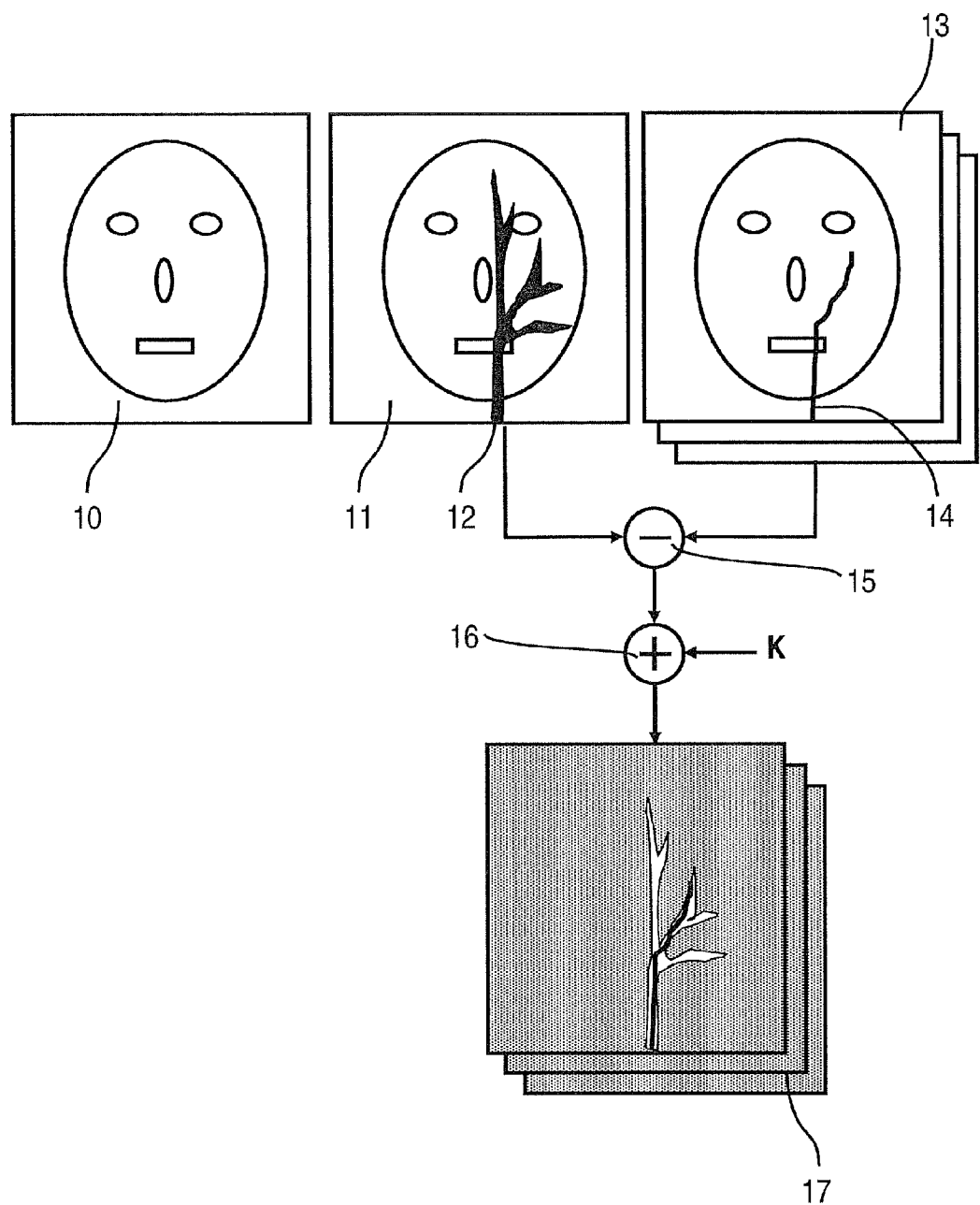
FIG. 2 shows a known roadmap method (state-of-the-art)

Instead of the usual subtraction (mask 11 from the fluoroscopy series 13), firstly (see also FIG. 2) the native image 10 is subtracted from the mask image 11 and a constant K is added, resulting in a first subtraction image 22 which by definition now only contains the vascular tree 12.

The first subtraction image 22 is subsequently processed further in the most diverse ways in order to form the vessel image 24:

reduction of noise in the image by means of suitable filtering techniques (e.g. low-pass).

reduction of image artifacts that are produced by movement of the patient or object between native image 10 and the resulting mask image 11 (e.g. by "leveling of islands").

The vascular tree is now grayscale-value-homogenized with the aim rather of reducing the contrast of very dark points in the vascular tree (generally at those points where the vessel has the greatest extent, therefore where the most contrast agent is and consequently the greatest attenuation, i.e. darkening, takes place) and rather of increasing the contrast at less dark points (smaller vessel structures). This method is applied only for pixels with a grayscale value significantly under the constant K. This ensures that grayscale values of the vessel and not noisy pixels are processed further in such a way. The vascular tree is "restored".

Moreover, the grayscale value window with which the vascular tree 12 is visualized can be adaptively selected. Since contrasts of different heights are produced in different procedures and vessels (thickness of the vessel, contrast agent dilution, blood flow, injection rate, etc.), the maximum blackening or lightness (in the case of the inverted DSA image) can be determined by extraction of the vascular tree and used as normalization for the windowing.

In addition the native image 10 is subtracted from the current fluoroscopy image 13 and the constant K is added so that a subtracted second subtraction image 27 is produced which ideally contains only the object 14.

Every second subtraction image 27 is subsequently processed in the most diverse ways, resulting in the object image 29.

Noise is reduced by means of suitable filter methods.

Image artifacts that have been produced by movement between the recording of the native image 10 and the recording of the fluoroscopy image 13 are reduced, e.g. by "leveling islands"—uncorrelated structures.

The object 14 is grayscale-value-homogenized. That is to say that the object 14 is imaged with higher or lower contrast through variation of the absorption and corresponding spectral changes in the X-ray spectrum at different points of the anatomy. Moreover the object 14 can be "restored", i.e. recognized as a geometric structure by means of a correlation analysis and amplified. Only specific structures such as wires (i.e. elongate shapes), balloons, coils, etc. that are typical of these procedures are permitted in this restoration.

The grayscale values of the extracted object 14 can also be used for adaptively controlling the grayscale value windowing. Depending on patient thickness etc., the object 14 can initially be represented with very different contrast. The wire contrast can be adjusted by means of the adaptive windowing.

The object 14 can be extracted from the second subtraction image 27 by means of simple threshold value forming, since the object 14 generates much darker grayscale values than the environment, which as a result of the mask subtraction yields a grayscale value that, except for noise or deviations generated by motion artifacts which can be reduced by suitable low-pass forming or other methods, is identical everywhere. Thus, as the object image 29 it would be possible to generate a binary object image 35 which enters a "0" where there is background, and a "1" where the object 14 is located.

Finally, the difference image, the vessel image 24, is subtracted from the current difference image, the object image 29, and a constant K added. This results in a roadmap image. This is performed for each image 13 ⇒ 27 ⇒ 29 ⇒ 33.

If a binary object image 35 of the object 14 was generated as the object image 29, during the merging of the images 24 and 35 in order to form the definitive roadmap image 33 all the pixels in the roadmap image 33 can now be replaced by a fixed low, i.e. dark or black, grayscale value at which the object 14 was extracted in the binary object image 35 of the object 14 (i.e. at those points where a "1" was entered). Irrespective of the local contrast of the vascular tree 12 which for the most diverse following reasons (i-v) yields grayscale values having different heights, i.e. light, the object 14 is thus rendered visible and no longer "disappears" due to the addition of light vessel background. The object 14 can thus be represented irrespective of i. global and local vessel thickness (anatomy),
ii. local X-ray absorption (the contrast is reduced behind bones, for example),
iii. selected dilution of the contrast agent,
iv. injection rate or, as the case may be, progression of the contrast in the vascular tree 12, and
v. chosen image processing parameters for vascular tree visualization. Points i, ii, iii all lead to a variation in the lightness of the vascular tree 12 or parts thereof.

To enhance its visibility the object 14 can also be represented in color. For that purpose, however, the monitor 9 must be a color monitor.

The method can also be used with a DSA image. In this case only the path on the right in FIG. 3 "13-10 ⇒ 27 ⇒ 29" is performed and a DSA image representing the vascular tree 12 is subtracted instead of the vessel image 24.

Furthermore, as already described, the overlay reference method can be improved. In contrast to the visualization which is described in the previous section and only represents the object 14 in the vascular tree 12, but no other anatomy, in this case, thanks to the extraction of the object 14, the latter can be overlaid on the fluoroscopy image 13 and for that purpose the inverted DSA image blended at a given percentage.

In this case—analogously to the roadmap method—the native image 10 from the DSA sequence can be used for subtracting the fluoroscopy series 13. From this difference, which again represents only the object 14, a grayscale value representation of the object 14 that is independent of the vessel contrast or degree of blending of the DSA image or of a native image (unsubtracted DSA) can be generated by means of binary object extraction or segmentation. To that extent this method differs from the conventional overlay reference method in which the fluoroscopy image is not subtracted:

The object 14 can be extracted from the fluoroscopy series 13 subtracted with the DSA mask image (threshold value forming or segmentation).
The pure object image 29, 35 can now be overlaid on
a DSA image (vascular tree 12),
a native image 10 (original mask image) in order to visualize anatomy, or
a linear combination of DSA image and native image 10.

In this case the object 14, which is present in binary form, can again be overlaid with a high contrast that is independent of the remainder of the image.

Furthermore the method can also be combined with a 3D representation of the vascular tree 12. In this case the 3D representation of the vessel is displayed as vessel image 24 in the same projection and the same detail section as the image series 13 of fluoroscopy images and "fed in" in the last step of subtraction of object image 29 or binary image 35 and vessel image 24.

In a third alternative for the roadmap method a more complex image processing step, a selection method according to the aforementioned rules, takes place instead of the subtraction shown in FIG. 3.

The improved visualization of the object 14 in the vascular tree 12 is ensured by the various image processing steps, in particular of the grayscale value homogenization both of the vascular tree 12 and of the object 14. "Burnout", i.e. the disappearance of the wire in the white vessel, is avoided.

Moreover with this method the object 14 can be "restored", i.e. the contrast increased where it has been detected as a weaker or "collapsed" signal due, for example, to noise or a different spectrum.

Since the different images that are processed with one another are produced at different times, slight displacements or distortions from image to image can possibly result due, for example, to movements of the patient or table. Accordingly, at each point at which at least two images are processed with one another in each case in order to generate a new image, i.e.

during the generation of the mask, the first subtraction image 22,
during the generation of the native-image-corrected fluoroscopy images, the second subtraction images 27, and
during the final subtraction of the images 24 from 29 or 35 in order to generate the roadmap images 33, possible motion artifacts can be corrected by means of what are termed pixel shift methods. Such pixel shift methods are well-known and are to be cited as well herewith explicitly only as a component part of the image processing.

The invention claimed is:

1. A method for improving a visualization of an object in an interventional angiographic examination, comprising:
acquiring an empty image with pure anatomy, a filling image with vascular tree filled with a contrast agent, and a native image with the object being introduced by a detector of an imaging recording system, the empty image, the filling image, and the native image having a matrix-shaped array of pixels;
subtracting the empty image from the filling image for generating a first subtraction image by an image processing system;
subtracting the empty image from the native image for generating a second subtraction image by the image processing system;
processing the first subtraction image for generating a vessel image by the image processing system;
processing the second subtraction image for generating an object image by the image processing system;
processing the vessel image and the object image for generating a roadmap image by the image processing system; and
playing the roadmap image on a monitor,
wherein the vessel image is subtracted from the object image for generating the roadmap image.

2. The method as claimed in claim 1, wherein the first and the second subtraction image is processed by a filtering operation comprising sharpening, edge enhancement, and/or grayscale value processing.

3. The method as claimed in claim 1, wherein the vessel image and the object image is processed by a pixel by pixel selection with a sorting pass.

4. The method as claimed in claim 3, wherein the roadmap image is processed after the sorting pass for enhancing contrast, suppressing noise, and/or increasing sharpness.

5. The method as claimed in claim 1, wherein the second subtraction image is processed by a binary operation comprising generating a threshold value or a segmentation.

6. The method as claimed in claim 1, wherein an addition of a constant is performed after generating the first and the second subtraction image and the roadmap image.

7. The method as claimed in claim 1, wherein the method is a roadmap method.

8. The method as claimed in claim 1, wherein a fluoroscopy image is overlaid over a digital subtraction angiography image.

9. The method as claimed in claim 1, wherein the vessel image and the object image are merged for generating the roadmap image having a fixed grayscale value.

10. The method as claimed in claim 9, wherein the fixed grayscale value is black or colored.

11. An angiographic X-ray system for improving a visualization of an object in an interventional angiographic examination, comprising:
   a C-arm;
   an X-ray emitter arranged on the C-arm;
   an X-ray detector arranged on the C-arm that acquires an empty image with pure anatomy, a filling image with vascular tree filled with a contrast agent, and a native image with the object being introduced, the empty image, the filling image, and the native image having a matrix-shaped array of pixels;
   an image processing system that:
      subtracts the empty image from the filling image for generating a first subtraction image by an image processing system,
      subtracts the empty image from the native image for generating a second subtraction image by the image processing system,
      processes the first subtraction image for generating a vessel image by the image processing system,
      processes the second subtraction image for generating an object image by the image processing system, and
      processes the vessel image and the object image for generating a roadmap image by the image processing system; and
   a monitor that plays the roadmap image,
   wherein the image processing system subtracts the vessel image from the object image for generating the roadmap image.

12. The angiographic X-ray system as claimed in claim 11, wherein the image processing system processes the second subtraction image by a binary operation comprising generating a threshold value or a segmentation for generating a binarily extracted object image.

13. The angiographic X-ray system as claimed in claim 12, wherein the image processing system overlays the vessel image over the binarily extracted object image.

14. The angiographic X-ray system as claimed in claim 11, wherein the vessel image and the object image is processed by a pixel by pixel selection with a sorting device.

15. The angiographic X-ray system as claimed in claim 11, wherein an addition of a constant is performed after generating the first and the second subtraction image and the roadmap image for setting a mean grayscale value.

\* \* \* \* \*